(12) United States Patent
Smith et al.

(10) Patent No.: US 9,078,730 B2
(45) Date of Patent: Jul. 14, 2015

(54) SURGICAL INSTRUMENT AND METHOD FOR THE TREATMENT OF URINARY INCONTINENCE

(71) Applicant: ETHICON, INC., Somerville, NJ (US)

(72) Inventors: Daniel J. Smith, Dayton, NJ (US); Steven Nguyen, North Brunswick, NJ (US); Michael Nordmeyer, Pittstown, NJ (US)

(73) Assignee: ETHICON, INC., Somerville, NJ (US)

( * ) Notice: Subject to any disclaimer, the term of this patent is extended or adjusted under 35 U.S.C. 154(b) by 356 days.

(21) Appl. No.: 13/790,594

(22) Filed: Mar. 8, 2013

(65) Prior Publication Data

US 2014/0257020 A1   Sep. 11, 2014

(51) Int. Cl.
| | |
|---|---|
| *A61F 2/02* | (2006.01) |
| *A61F 2/00* | (2006.01) |
| *A61B 17/06* | (2006.01) |
| *A61B 17/00* | (2006.01) |

(52) U.S. Cl.
CPC ......... *A61F 2/0045* (2013.01); *A61B 17/06109* (2013.01); *A61B 2017/00805* (2013.01); *A61B 2017/06009* (2013.01); *A61B 2017/06014* (2013.01)

(58) Field of Classification Search
None
See application file for complete search history.

(56) References Cited

U.S. PATENT DOCUMENTS

| | | |
|---|---|---|
| 5,899,909 A | 5/1999 | Claren et al. |
| 7,204,802 B2 | 4/2007 | De Leval |
| 7,261,723 B2 | 8/2007 | Smith et al. |
| 7,611,454 B2 | 11/2009 | De Leval |
| 2008/0132753 A1 | 6/2008 | Goddard |
| 2009/0306459 A1 | 12/2009 | De Leval |
| 2011/0106108 A1 | 5/2011 | Ostrovsky et al. |
| 2011/0230703 A1 | 9/2011 | Young et al. |

*Primary Examiner* — Charles A Marmor, II
*Assistant Examiner* — Shannon McBride

(57) ABSTRACT

A surgical assembly including a surgical introducer having a handle portion and a needle element extending to a free distal end, and a sliding mechanism including a compressible member and a sliding button slidably coupled to the handle portion for longitudinal movement relative thereto and having a first retaining device extending outwardly from a distal end and a projection extending outwardly to a position adjacent the compressible member. First and second sheath elements each have a proximal end, a closed tapered distal end region, a channel therein, and a side aperture at a predetermined distance from the distal tip. The needle element slidably extends through the side aperture and into the channel of the first sheath element. An implant having first and second ends is coupled to the proximal ends of the first and second sheath elements respectively. The sliding button is slidable between a first resting position and a second more distal position wherein the retaining element can engage the side aperture, and wherein when so engaged the compressible member exerts a constant force on the sliding button and sheath element in a direction toward the first resting position of the sliding button.

18 Claims, 9 Drawing Sheets

SURGICAL INSTRUMENT AND METHOD FOR THE TREATMENT OF URINARY INCONTINENCE

BACKGROUND OF THE INVENTION

1. Field of the Invention

The present invention relates generally to devices and methods for the treatment of female urinary incontinence, and more particularly, to an improved inserter and sheath combination particularly suitable for placing a sub-urethral sling.

2. Background Discussion

Women account for more than 11 million incontinence cases, with a majority of those women suffering from stress urinary incontinence (SUI). Women with SUI involuntarily lose urine during normal daily activities and movements, such as laughing, coughing, sneezing and regular exercise.

SUI may be caused by a functional defect or weakened tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. This patent discloses a surgical instrument comprising a shank having a handle at one end and connecting means at the other end to receive, one at a time, two curved needle-like elements which each are connected at one end to respective ends of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by Ethicon, Inc. of Somerville, N.J. In this procedure, two 5 mm needles pass a PROLENE mesh trans-vaginally and through the abdomen to create a tension-free support under the mid-urethra.

Sub-urethral slings have also been placed by a different approach wherein a needle is passed first though the abdominal wall along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has more recently been developed in which the implanted sling extends from beneath the urethra out through the obturator hole on either side. This "transobturator" procedure may involve inserting an appropriately configured needle from a vaginal incision and subsequently out through the obturator hole, or vice versa. The former technique (an "inside-out" approach) and associated instruments are described in detail in U.S. Pat. Nos. 7,611,454, 7,204,802, and 7,261,723, and U.S. Patent Publication No. 2009/0306459, which are incorporated herein by reference in their entirety. As illustrated in U.S. Pat. No. 7,261,723, this technique may be performed using a surgical instrument including a surgical passer or introducer and tube elements applied over the ends of the surgical passers that are coupled to the tape to be implanted under the urethra.

One problem associated with products including a combination surgical passer and tube or sheath element is ensuring a proper fit between the surgical passer and tube element so that the tube element (which is coupled to the implant) is suitably secured to the surgical passer throughout the procedure, but can be readily removed from the surgical passer after it has been properly passed through the body to allow final placement of the implant. Previously known devices had either relied exclusively on a frictional or interference fit between the two pieces along at least a portion of their respective lengths, and/or some type of complementary interlocking recess/projection along their respective lengths of the type described in the '723 patent. For devices that rely exclusively on a frictional fit, they can either be subject to relative movement during the procedure if the friction connection is too weak, or otherwise be difficult or cumbersome for a surgeon to separate following passage of the surgical passer through the body. A complementary interlocking recess/projection requires a unique surgical passer and tube design that adds to the manufacturing and device costs of the product.

In an effort to overcome these disadvantages, one known device described in U.S. Patent Publication No. 2011/0230703, which is incorporated herein by reference in its entirety, discloses a simplified mechanism by which to secure the sheath element to a retaining device. The device described in this publication is also commercially available under the name GYNECARE TVT EXACT®, which is manufactured and sold by Ethicon, Inc. of Somerville, N.J. The retaining device of this known instrument is static resulting in a predetermined positioning of the distal end of the needle element relative to the distal end of the sheath element. It has been found, however, that improper use of this device (i.e., exposing the device to increased external force during passage through the body) can result in deformation of the tissue penetrating tip of the sheath element.

Thus, it would be desirable to provide a surgical assembly having improved resistance against such external forces at the distal end of the instrument.

SUMMARY OF THE INVENTION

The present invention provide a surgical assembly including a surgical introducer having a handle portion and a needle element extending outwardly from the handle portion to a free distal end, and a sliding mechanism including a compressible member positioned within the handle portion and a sliding button slidably coupled to the handle portion for longitudinal movement relative thereto. The sliding button has at least a first retaining device extending outwardly from a distal end thereof and a projection extending outwardly therefrom to a position substantially adjacent to a proximal end of the compressible member. The assembly also includes substantially identical first and second sheath elements each having a proximal end, a tapered distal end region terminating in a closed tissue penetrating distal tip, a channel extending therein from an opening at the proximal end to the closed distal tip, and a side aperture defined by a peripheral edge positioned at a predetermined distance from the distal tip and extending into the channel. The needle element of the introducer extends through the side aperture and into the channel of the first sheath element so as to be slidably engaged therewith. The assembly further includes an implant made of a substantially flat, flexible, biocompatible material, and having first and second ends coupled to the proximal ends of the first and second sheath elements respectively. The sliding button is slidable between a first resting position wherein the compressible member does not exert any force on the projection of the sliding button and wherein the predetermined distance between the distal tip and side aperture of the first sheath element is such that the retaining device cannot engage the peripheral edge of the side aperture; and a second more distal position wherein the retaining element can engage the peripheral edge of the side aperture, and when so engaged the compressible member exerts a constant force on the sliding button and sheath element in a direction toward the first resting position of the sliding button.

The retaining device of the assembly may project outwardly and in a direction toward a proximal end of the handle.

In one embodiment, the needle element has an outer diameter of approximately 3.0 mm and the channel of the sheath element has a diameter of approximately 3.2 mm. In yet another embodiment, the sheath element has an outer diameter of approximately 4.2 mm.

In yet another embodiment, the needle element has a tapered distal end region that is positioned within the tapered distal end region of the sheath element. The tapered distal end region of the needle portion may have a length of approximately 1-10 mm. The tapered distal end region of the sheath element may further have a length of approximately 3-5 mm.

According to yet another embodiment, the needle element is made of stainless steel and the sheath element is made of a medical grade plastic selected from the group consisting of urethane, polyethylene, and polypropylene.

In yet another embodiment, the needle element of the introducer has a contour, and the sheath element follows the introducer contour.

Also provided is a method for treating stress urinary incontinence in a woman, including the steps of obtaining a surgical assembly including a surgical introducer having a handle portion and a needle element extending outwardly from the handle portion to a free distal end, and a sliding mechanism including a compressible member positioned within the handle portion and a sliding button slidably coupled to the handle portion for longitudinal movement relative thereto. The sliding button has at least a first retaining device extending outwardly from a distal end thereof, a projection extending outwardly therefrom to a position substantially adjacent to a proximal end of the compressible member, and substantially identical first and second sheath elements each having a proximal end, a tapered distal end region terminating in a closed tissue penetrating distal tip, a channel extending therein from an opening at the proximal end to the closed distal tip, and a side aperture defined by a peripheral edge positioned at a predetermined distance from the distal tip and extending into said channel. The method further includes the step of inserting the needle element into the channel of the first sheath element through the side aperture such that the distal end of the needle element is positioned within the distal end region of the first sheath element, exerting pressure on the slidable button to move the slidably button against the compressible member from a first resting position wherein the compressible member does not exert any force on the slidable button to the second more distal position wherein the compressible member exerts a constant force on the slidable button, engaging the retaining device with the peripheral edge of the side aperture of the first sheath element to thereby removably couple the sheath element to the introducer, and releasing pressure on the slidable button to thereby allow the compressible member to exert a constant force on the slidable button and first sheath element in a direction toward the first resting position.

According to one embodiment, the retaining device projects outwardly and in a direction toward a proximal end of the handle. The needle element may further have an outer diameter of approximately 3.0 mm and the channel of the sheath element may have a diameter of approximately 3.2 mm, and the sheath element may further have an outer diameter of approximately 4.2 mm.

In yet another embodiment, the needle element has a tapered distal end region and the inserting step further includes inserting the needle element until the tapered distal end region of the needle element is positioned within the tapered distal end region of the sheath element.

In alternate embodiments, the tapered distal end region of the needle portion may have a length of approximately 1-10 mm, and/or the tapered distal end region of the sheath element may have a length of approximately 3-5 mm.

In yet another embodiment, the needle element is made of stainless steel and the sheath element is made of a medical grade plastic selected from the group consisting of urethane, polyethylene, and polypropylene.

In yet another embodiment, the needle element of the introducer has a contour, and the sheath element follows the introducer contour.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
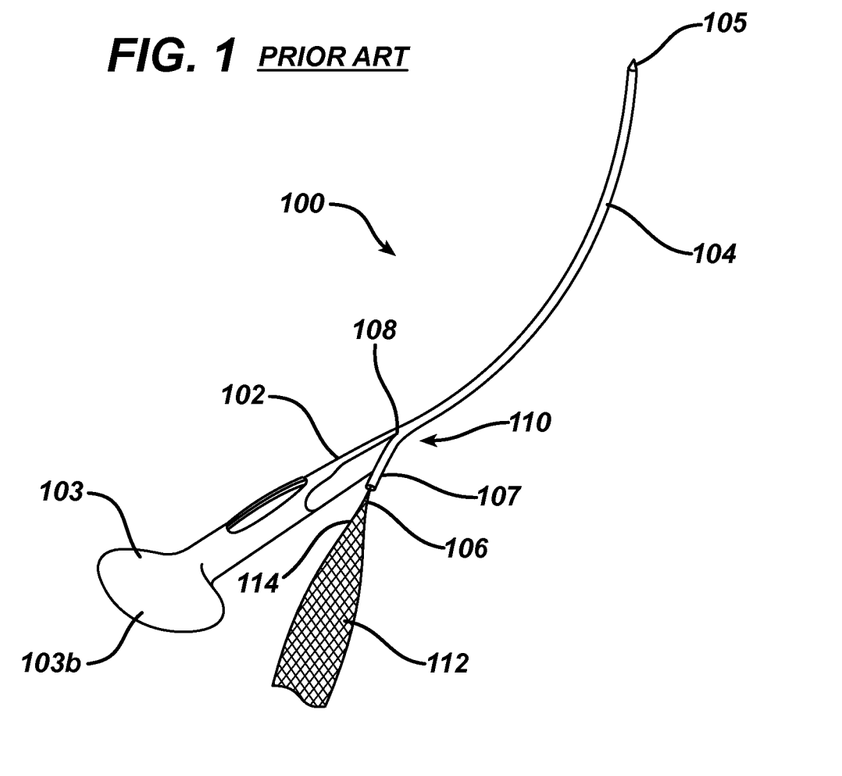
FIG. 1 illustrates in general a surgical assembly into which the present invention can be incorporated.
Figure 2:
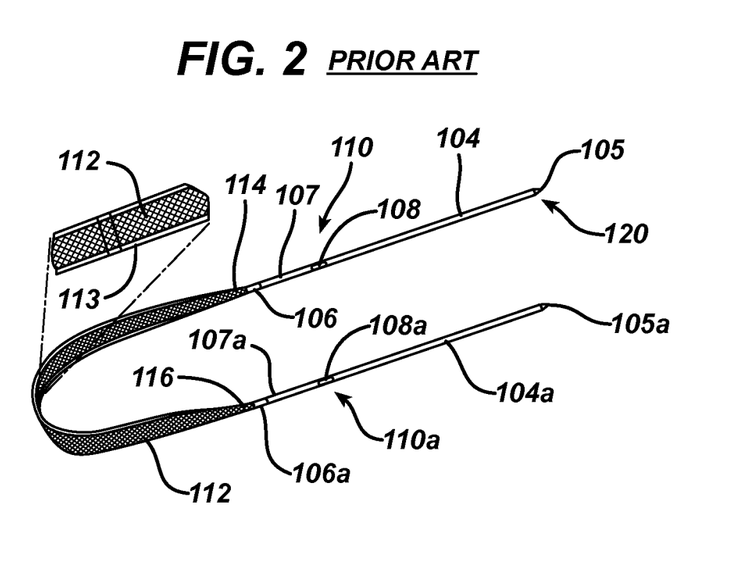
FIG. 2 illustrates separately the introducer and sheath of the surgical assembly of FIG. 1.
Figure 3:
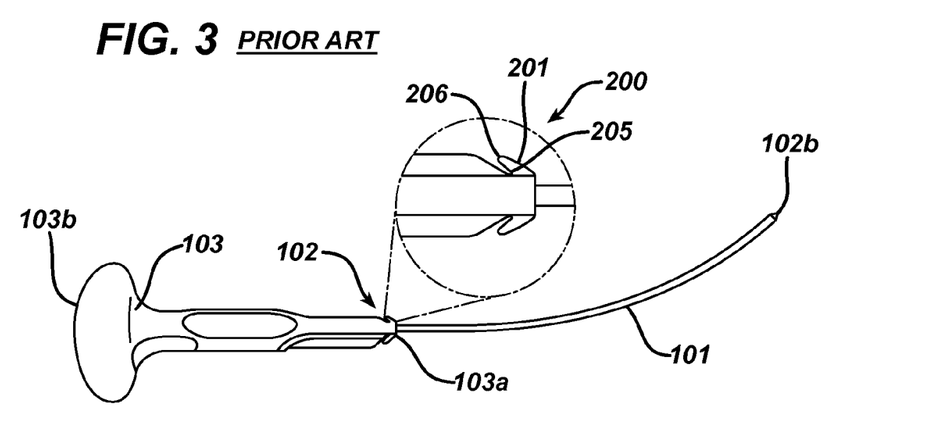
FIG. 3 illustrates in greater detail one mechanism for securing the introducer to the sheath in the assembly of FIG. 1.

FIGS. 1-3 illustrate generally a surgical assembly of a known type into which the inventive features described further below may be incorporated. The surgical assembly 100 includes an introducer 102 having needle element 101 and a handle portion 103 having a proximal end 103b and a distal end 103a, and first and second sheath elements 104, 104a. The needle element extends outwardly from the handle to a distal end 102b. The sheath elements are tube type elements each having a tapered distal end region 120 terminating in a close tissue penetrating distal tip 105, 105a and a channel extending from an opening 106, 106a at the proximal end 107, 107a to the closed distal tip 105, 105a. As illustrated more clearly in FIG. 2, the sheath elements 104, 104a also each include a side hole or aperture 108, 108a in one side thereof in the proximal end region 110, 110a. A biocompatible tape or mesh 112 to be implanted beneath the urethra of a patient includes first 114 and second 116 ends which are secured respectively to the proximal ends 107, 107a of the sheath elements as shown in FIG. 2. Preferably, the ends are inserted into the proximal end openings 106, 106a of the sheath elements and heat and pressure is applied to fixedly join the two. The mesh implant 112 is preferably substantially enclosed within a thin polyethylene sheath 113 as shown in the enlarged portion of FIG. 2. The polyethylene sheath may include two separate sheath portions applied over both ends and overlapping in the middle region so that, following implantation of the mesh, they can readily be removed from respective ends of the mesh. In one embodiment, the mesh implant is a polypropylene mesh, but the implant may be comprised of any suitable biocompatible material.

The sheath element channels have an inner diameter dimensioned to receive therein the needle element 101 of the introducer 102. Preferably, the surgical assembly includes a single introducer that is receivable within both the first and second sheath elements channels, although a second introducer could also be provided in the surgical assembly.

The outer diameter of the needle element 101 of the surgical introducer 102 is designed relative to the inner diameter of the channel of the sheath or tube element so that the surgical passer is readily insertable within the tube element, and removably therefrom with little frictional resistance. In this manner, following passage of the surgical assembly through the body as described below, the introducer can readily be removed from the sheath element without moving or otherwise disturbing the position of the sheath element and attached implant. In a preferred embodiment, the outer diameter of the needle element is approximately 3 mm and the inner diameter of the sheath is approximately 3.2 mm. In a preferred embodiment, the sheath element is made of a high density polyethylene (plastic) material that allows the sheath to conform to necessary applied forces without loss of intended function, and still return to its approximate original shape.

As the introducer is so readily removable/slidable relative to the sheath element, the surgical assembly of this known device further includes a retaining device 200 to ensure that the sheath elements 104, 104a can be fixedly, but removably secured to the introducer 102 during passage of the surgical assembly through the body. The retaining device 200 illustrated in FIG. 3 includes one or more projections 201 extending outwardly from the introducer, and in the illustrated embodiment from the handle portion of the introducer. The projection(s) 201 are located along the length of the introducer at a position where, when the sheath element 104 is slidably received over the needle element 101 as shown in FIG. 3, it is substantially aligned with the side aperture 108 of the sheath element. In this manner, the projection 201 can be inserted into the side aperture to engage the edge or periphery defining the side aperture to thereby hold the sheath in place relative to the introducer. In a preferred embodiment, the retaining elements project both outwardly and also in a direction towards the proximal end 103b of the introducer. This enables the retaining element to more securely grasp the sheath element and prevent it from slipping off the distal end of the needle element.

With this prior art device, however, the length of the sheath relative to the length of the needle element has to have enough slack to enable the side aperture of the sheath to be pulled over the projection of the retaining device to engage the two components. In practice, once the side aperture clears the distal most edge 206 of the projection 201 (see FIG. 3), the sheath element is free to move in the proximal direction until it comes to rest engaging the inner apex 205 of the projection. Further, it has been found that users affirmatively urge the sheath element to this position to ensure themselves that the two are properly and securely engaged. As a consequence, the distal end of the needle element 102b could be set back slightly from the tissue penetrating distal end of the sheath element that surrounds it, leaving the very distal end of the sheath element with no other structural support within it, somewhat analogous to an "empty straw." If the device is not used properly, the distal end region of the sheath element can be subject to bending deformation.

Figure 5A:
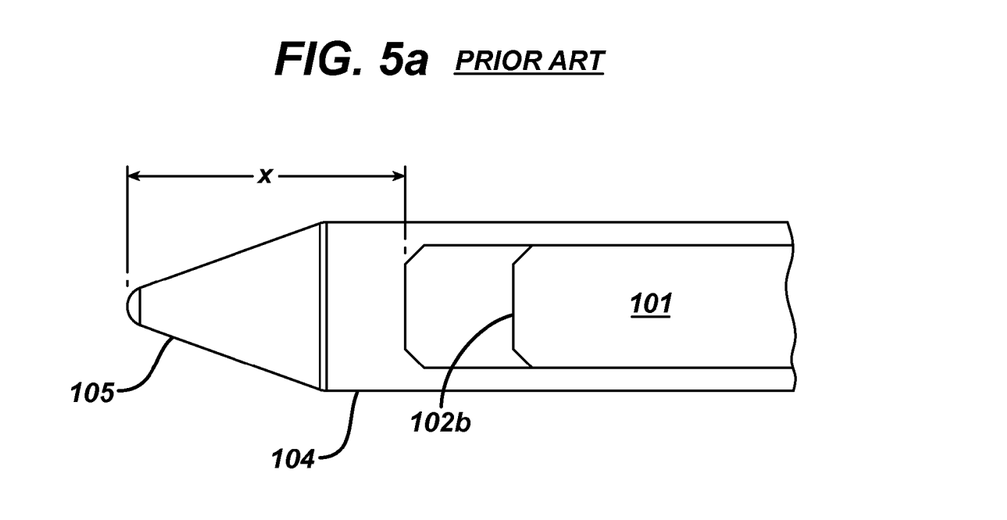
FIG. 5a illustrates the distal tip of an introducer relative to the distal end of a sheath in a prior art device.
Figure 5B:
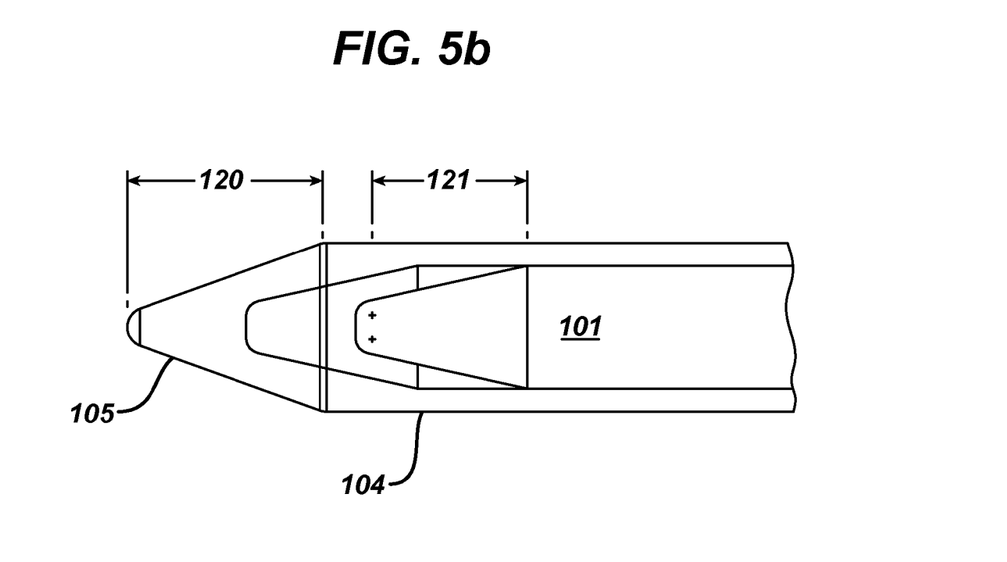
FIG. 5b illustrates the distal tip of an introducer according to the present disclosure relative to the distal end of a sheath.
Figure 6A:
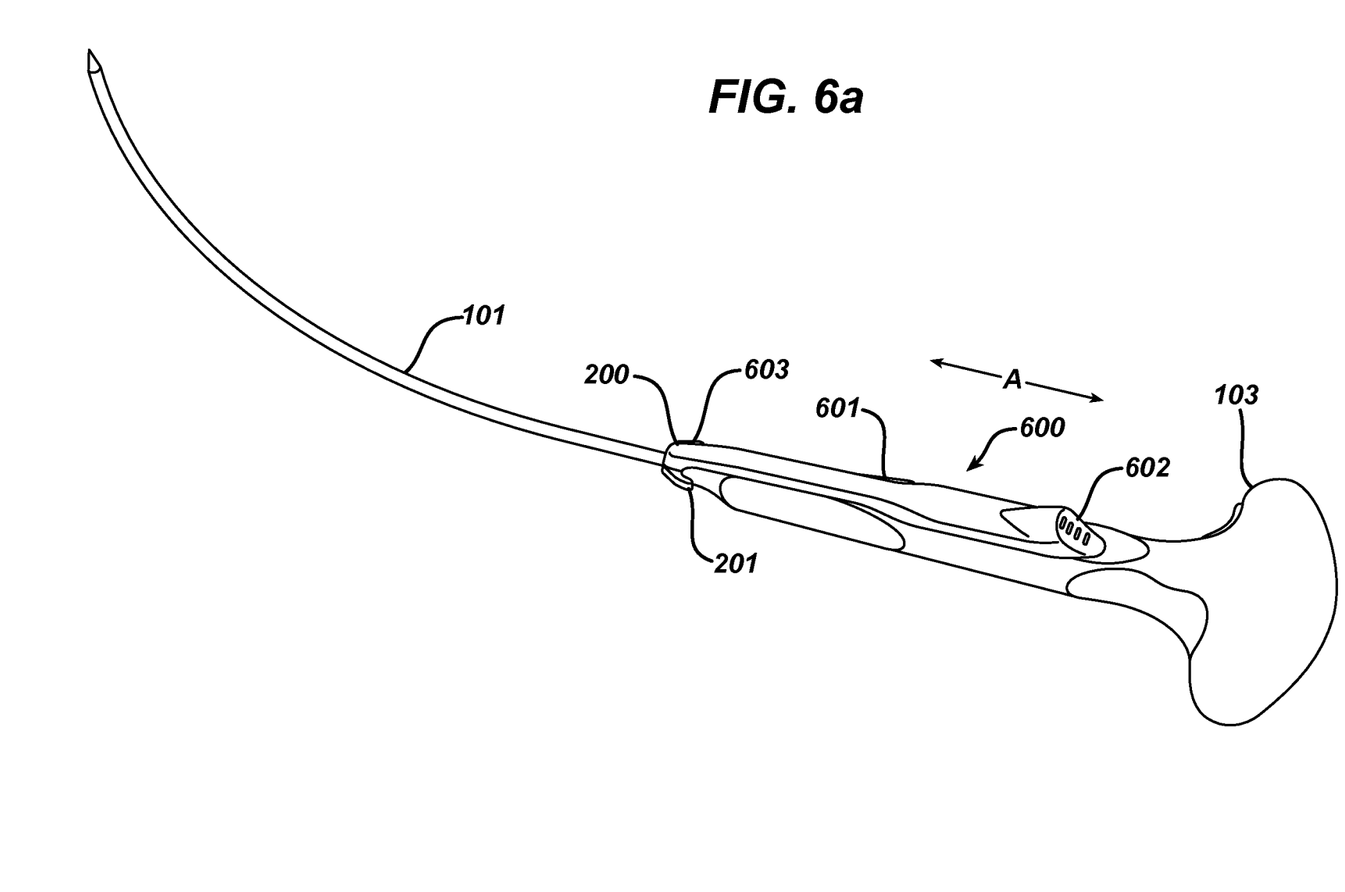
FIGS. 6a-6c illustrate one embodiment according to the present invention of a sliding mechanism for securing the sheath to the introducer.
Figure 6B:
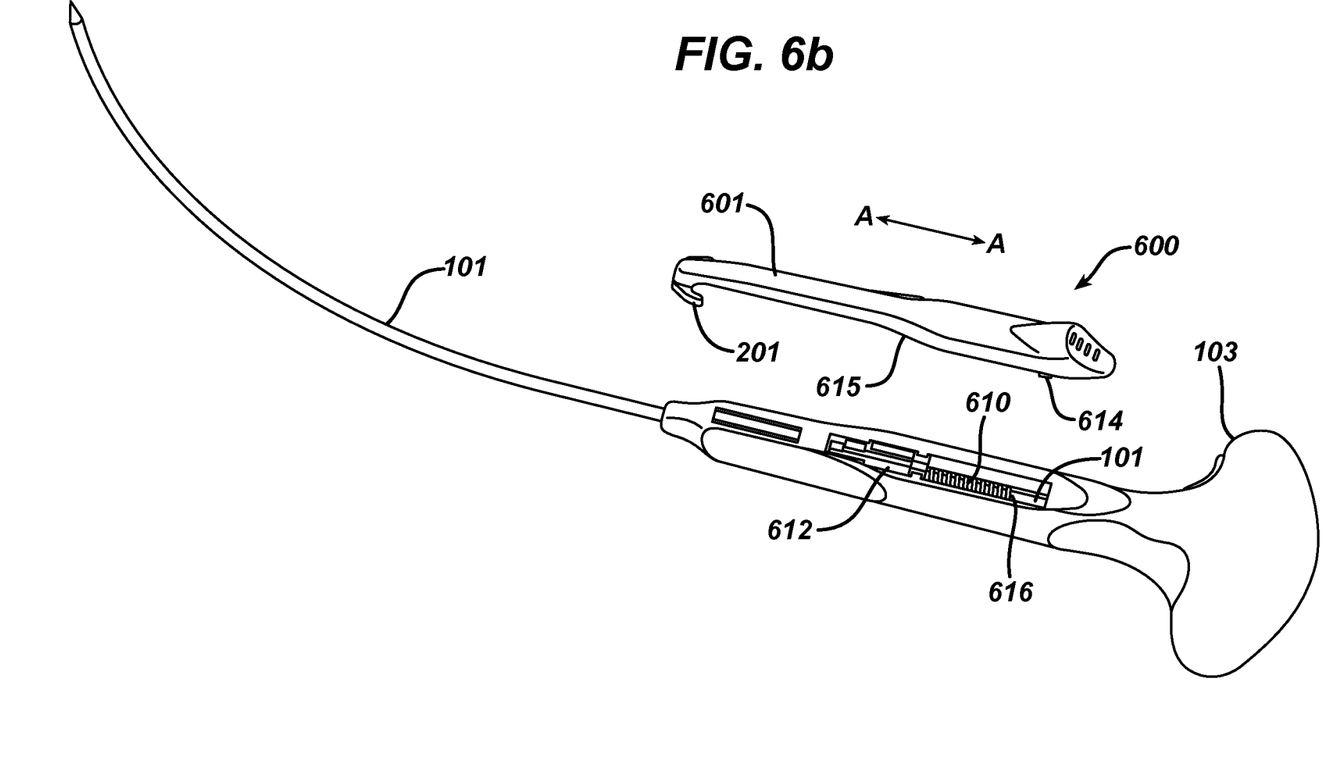

The device according to the present invention includes various features illustrated in detail in FIGS. 5, 6a-6c and 7a-7b that better enable the assembly to resist such deformation. Referring now to FIGS. 6a and 6b, the surgical assembly of the present invention includes a sliding mechanism 600 which includes a sliding button 601 that can slide longitudinally relative to the handle 103 and attached needle element 101 in the directions indicated by arrows A in FIG. 6a. The proximal end 602 of the sliding button 601 is configured in any suitable manner to readily engage a user's thumb or finger so that pushing on the proximal end 602 causes the sliding button to move toward the distal end as will be described further below. The distal end 603 of the sliding button includes a retaining device 200 such as that described above in connection with the prior art device.

Referring now to FIG. 6b, the needle element extends into the handle 103 as shown and as will be described in more detail below. A compressible member 610 such as a spring or the like is positioned within the handle portion 103 and in a preferred embodiment around the needle element near its proximal end as illustrated. A stop element 612 is positioned adjacent and distal to the spring element 610. The stop element can be of any suitable form and configuration that functions as a stop against which the spring is compressed as the sliding button is slid in the distal direction. In this particular embodiment, the stop element is U-shaped member shown in FIG. 6c, which is placed over the needle element and welded in place to secure the needle element to the handle with respect to both longitudinal movement and torsional movement. The sliding button includes a projection 614 that extends downwardly from its bottom surface 615, and is also preferably a U-shaped member sized and shaped for a snap fit against the needle element as shown best in FIG. 6c and positioned so as to rest against the proximal end 616 of the compressible member 610 in its uncompressed state. In the configuration illustrated in FIG. 6c, the sliding button is positioned in its most proximal, resting position. When a suitable amount of force is applied to the proximal end 602 of the sliding button 601, the spring force is overcome and the sliding button moves distally. The spring constant is selected so that when the retaining device engages the sheath element as will be described below and the user removes the applied force from the sliding button, a constant force is maintained on the sheath element to pull it toward the proximal end of the handle.

Figure 6C:
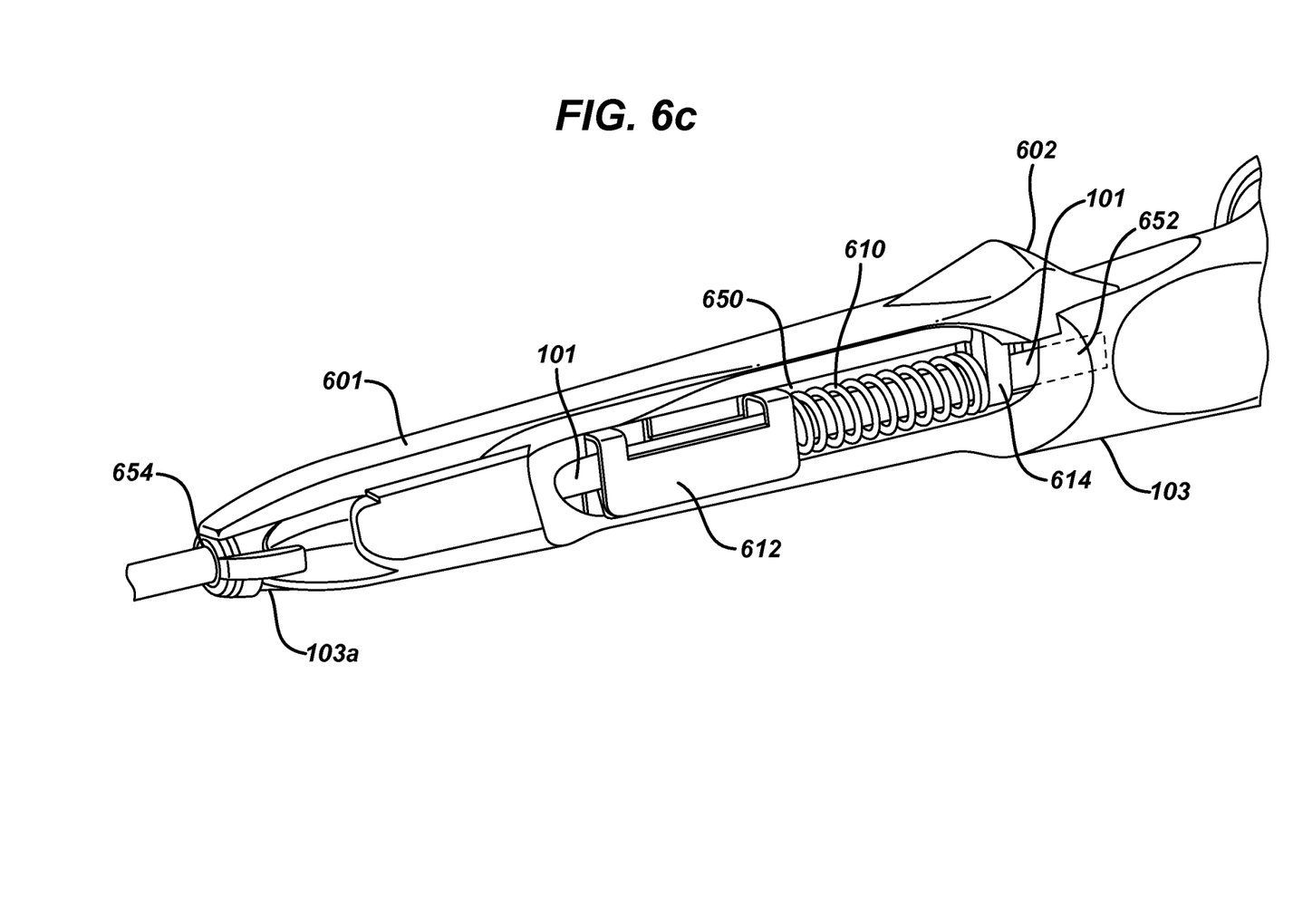

The handle portion 103 is preferably injection molded, and the device assembled as further described with particular reference to FIG. 6c. The needle element 101 is inserted through an opening (not shown) at the distal end 103a of the handle portion 103 and into a recess 652 within the molded handle shown in dotted lines on FIG. 6c. During insertion while the needle element is passing through the open channel 650 in the handle portion, it is threaded through compressible member 610 before being inserted into the recess 652. The stop member 612 is then placed over the needle element at a location distal, but adjacent to, the compressible member when the compressible member is in the uncompressed state as shown. The needle is then rotated into the proper position relative to the handle, and the stop member welded to the needle element so as to fixedly secure the needle element against both rotational and longitudinal movement relative to the handle portion. Thus, the stop element now also forms a "back stop" against which the compressible member can be compressed as described further below. Next, an aperture 654 in the distal end of the sliding button 601 is placed over the distal end of the needle element and slid down over the handle portion. Projection 614 is then snap fitted over the needle element 101 to couple the sliding button to the needle element and handle portion.

Figure 7A:
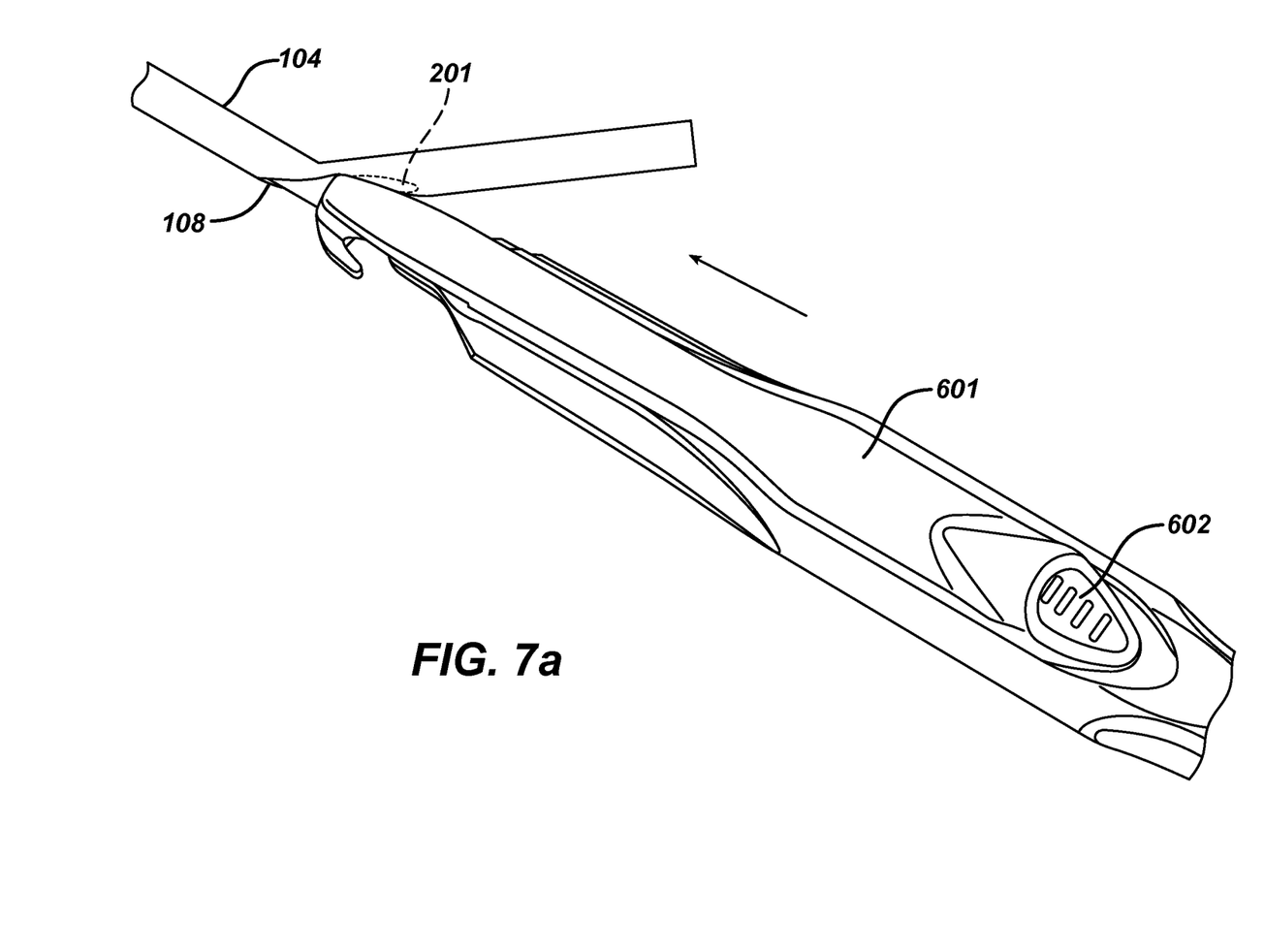
FIGS. 7a-7b illustrate the use of the sliding mechanism of FIGS. 6a-6c to secure the sheath to the introducer.
Figure 7B:
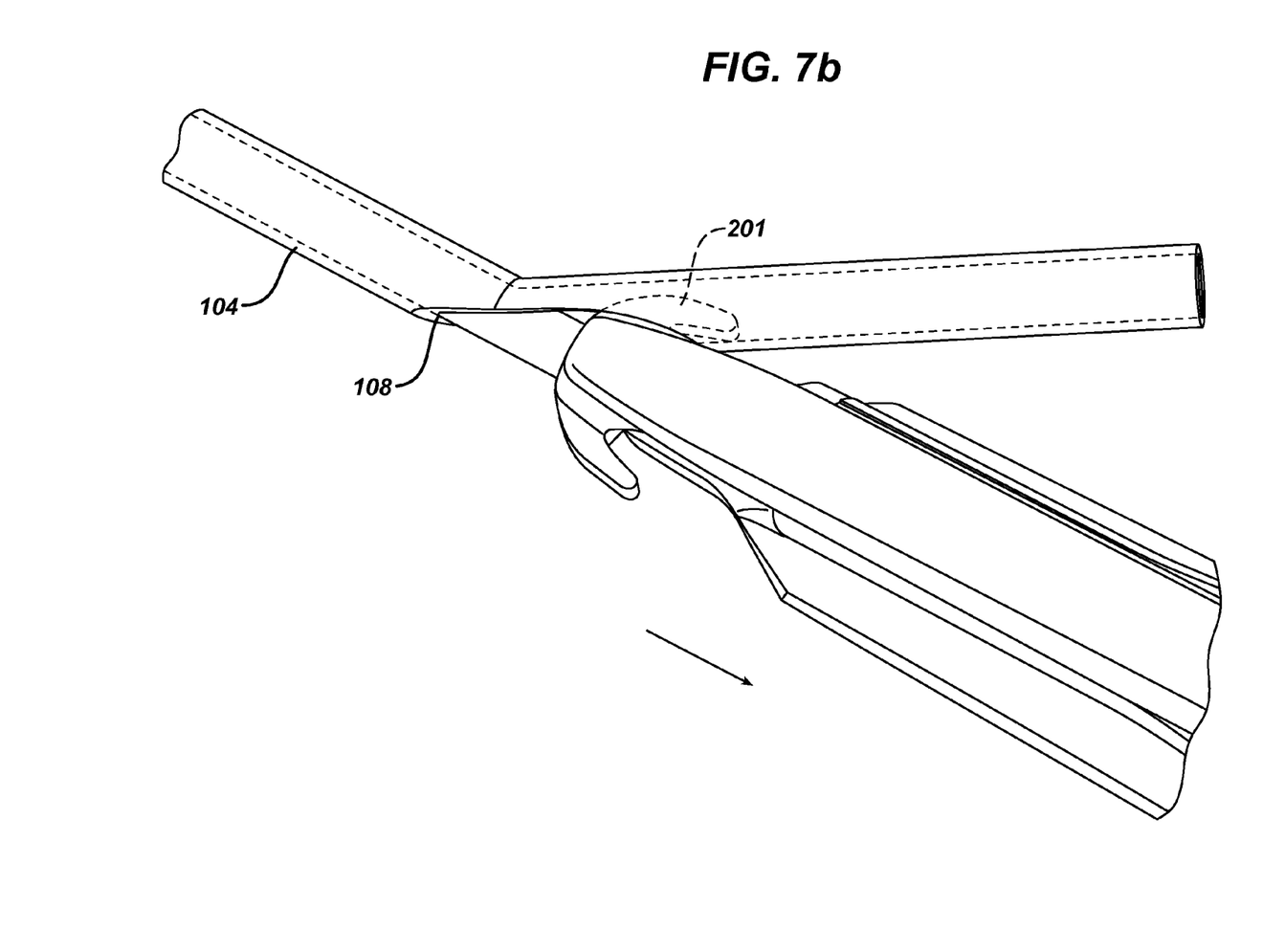

Referring now to FIGS. 7a-7b, following insertion of the needle element into the sheath as described above, the sliding button 601 is forced distally in the direction shown by the arrow in FIG. 7a by the user pushing on the proximal end 602 of the sliding button. At the same time, the sheath element is pulled in the opposite direction until the side aperture 108 is positioned entirely over the projection 201 of the retaining device 200 as shown in FIG. 7b. The user then releases pressure on the sliding button, at which time the compressible member exerts force against the projection of the sliding button 601 to urge the sliding button proximally toward its resting position as shown by the arrow in FIG. 7b. As indicated previously, the spring constant is selected so that when the sheath element is fully engaged the sliding button cannot fully return to its resting position, ensuring that the retaining element fully engages and exerts rearward pressure on the sheath element. In this manner, the distal end of the sheath element is constantly urged toward the distal end of the needle element ensuring that the distal end of the sheath element is better structurally supported at all times and less prone to bending or distorting when in use.

The surgical assembly described herein may also include another mechanism for increasing the ability of the distal end of the sheath element to resist bending and deformation. As illustrated in FIG. 5a, the prior art device included a sheath element having a tissue penetrating distal end 105, and a blunt needle element distal end 102b. This configuration leaves the entire length X of the distal end of the sheath element unsupported, and thus less able to resist bending forces and the like as the surgical assembly was passed through the body during a surgical procedure. The configuration illustrated in FIG. 5b greatly reduces the likeliness of this problem by providing more structural support to the distal end of the sheath element. As shown, the distal end of the needle element has a tapered distal end region 121 as opposed to the blunt configuration shown in FIG. 5a. This tapered distal end region 121 somewhat follows the contour of the tapered distal end region 120 of the sheath element 104, and further extends to within the sheath tapered distal end region 120 when the needle element is fully inserted within the sheath element as shown by the dotted lines in FIG. 5b. In this manner, the tapered distal end region 120 of the sheath element is much better suited to withstand any bending or moment forces.

Figure 4A:
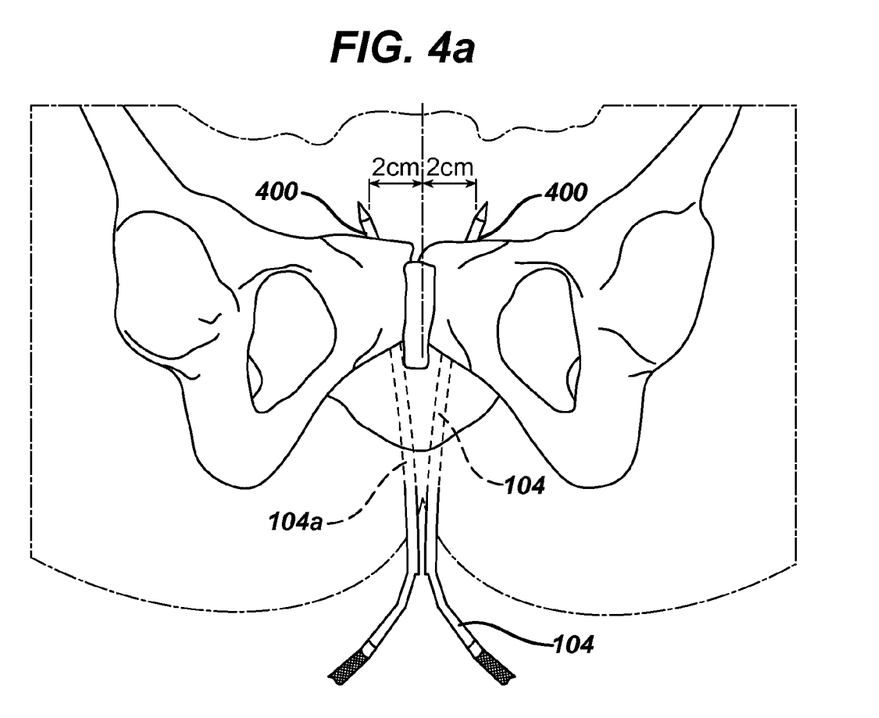
FIGS. 4a-4c illustrate an exemplary passage through the body of the surgical assembly of FIG. 1.
Figure 4B:
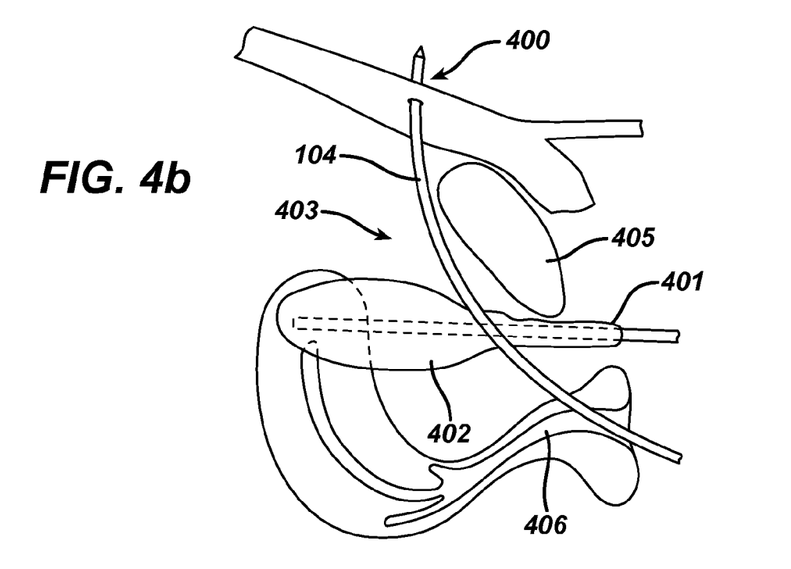
Figure 4C:
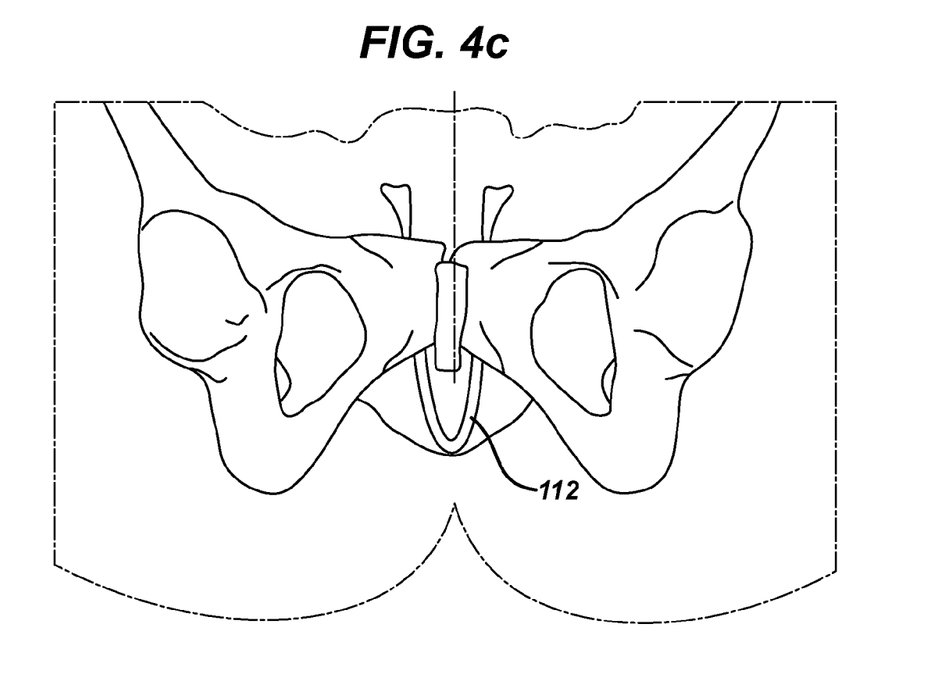

A method of using the above-described surgical instrument will now be described in detail with reference to FIGS. 4a-4c. The patient is placed in the lithotomy position with the hips flexed and the bladder emptied. A small paraurethral incision is made at the mid-urethra to position the tip of the sheath element. A sagittal incision is then made about 1.5 cm in length starting at approximately 1.0 cm cephalad from the urethral meatus. The incision will be positioned at the mid-urethral zone and will allow for subsequent passage of the implant. Two small paraurethral dissections (approximately 0.5 cm) are then made to accommodate the tips of the sheath elements of the surgical assembly.

The two exit points 400 are then identified and marked. These exit points should be 2-2.5 cm on each side of the mid-line, immediately above the pubic symphasis as shown in FIG. 4a. These exit points should be no more than 2.5 cm from the mid-line to avoid the inferior epigastric vessels, and near the mid-line and close to the superior aspect of the pubic bone 405 to avoid anatomic structures in the inguinal area and lateral pelvic sidewall.

Once the bladder is drained a catheter guide or the like 401 can be used to allow contra-lateral displacement of the bladder 402, bladder neck and urethra away from the tip of the surgical assembly as it is passed through the retropubic space 403.

One of the sheath elements 104 is then slidably engaged over the needle element 101 of the introducer 102, and the side aperture of the sheath element engaged with the retaining element in the manner described above with reference to FIGS. 7a-7b. After ensuring lateral displacement of the bladder with the catheter guide, the handle of the surgical assembly is held and the tip of the surgical assembly is passed paraurethrally through the urogenital diaphragm at the level of the midurethra. Initial insertion of the surgical assembly is controlled by using the tip of the index finger, which is placed in the vagina 406 under the anterior vaginal wall, just lateral to the suburethral incision. With the curved part of the assembly resting in the palm of the hand, the assembly is passed through the urogenital diaphragm into the retropubic space. The tip is then guided through the retropubic space staying as close as possible to the back of the pubic symphysis or pubic bone 405 until the tip reaches the abdominal exit point 400 as shown in FIGS. 4a and 4b.

The tip of the surgical assembly is then grasped and held in place with a suitable clamp or other instrument, and the sheath element is disengaged from the introducer by uncoupling the sheath element from the retaining device. This is accomplished by moving the sliding button 601 distally against the compressive force of the compressible member 610 to thereby release the force of the retaining device on the side aperture of the sheath element and allow the aperture to be readily removed from the projection 201 of the retaining device 200. The introducer is then retracted and removed from the body while leaving the sheath element in place within the body as shown in FIG. 4a. The procedure is then repeated on the other side of the body, and with the sheath elements in place in the body (before final placement of the implant), the catheter is removed and bladder integrity confirmed.

Both sheath elements are then pulled entirely through the abdominal exit points so that the implant is placed under the mid-urethra, and the implant cut in proximity to the sheath elements. The implant is then adjusted in a well known manner, the polyethylene sheaths removed from the ends of the implant, and the implant cut in proximity to the abdominal exit points. The vaginal incision and abdominal incisions are then closed and the implant left in place as illustrated in FIG. 4c.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical assembly comprising:
   a surgical introducer having a handle portion and a needle element extending outwardly from the handle portion to a free distal end, and a sliding mechanism including a compressible member positioned within the handle portion and a sliding button slidably coupled to the handle portion for longitudinal movement relative thereto, the sliding button having at least a first retaining device extending outwardly from a distal end thereof, the first retaining device including a projection extending outwardly therefrom to a position substantially adjacent to a proximal end of the compressible member; substantially identical first and second sheath elements each having a proximal end, a tapered distal end region terminating in a closed tissue penetrating distal tip, a channel extending therein from an opening at the proximal end to the closed distal tip, and a side aperture defined by a peripheral edge positioned at a predetermined distance from the distal tip and extending into said channel, the needle element of the introducer extending through the side aperture and into the channel of the first sheath element so as to be slidably engaged therewith; and
   an implant comprised of a substantially flat, flexible, biocompatible material, and having first and second ends coupled to the proximal ends of the first and second sheath elements respectively;
   wherein the sliding button is slidable between a first resting position wherein the compressible member does not exert any force on the projection of the sliding button and wherein the predetermined distance between the distal tip and side aperture of the first sheath element is such that the retaining device cannot engage the peripheral edge of the side aperture; and a second more distal position wherein the retaining element can engage the peripheral edge of the side aperture, and wherein when so engaged the compressible member exerts a constant force on the sliding button and sheath element in a direction toward the first resting position of the sliding button.

2. The surgical assembly according to claim 1, wherein the retaining device projects outwardly and in a direction toward a proximal end of the handle.

3. The surgical assembly according to claim 2, wherein the needle element has an outer diameter of approximately 3.0 mm and the channel of the sheath element has a diameter of approximately 3.2 mm.

4. The surgical assembly according to claim 3, wherein the sheath element has an outer diameter of approximately 4.2 mm.

5. The surgical assembly according to claim 1, wherein the needle element has a tapered distal end region that is positioned within the tapered distal end region of the sheath element.

6. The surgical assembly according to claim 5, wherein the tapered distal end region of the needle portion has a length of approximately 1-10 mm.

7. The surgical assembly according to claim 5, wherein the tapered distal end region of the sheath element has a length of approximately 3-5 mm.

8. The surgical assembly according to claim 5, wherein the needle element is comprised of stainless steel and the sheath element is comprised of a medical grade plastic selected from the group consisting of urethane, polyethylene, and polypropylene.

9. The surgical assembly according to claim 1, wherein the needle element of the introducer has a contour, and wherein the sheath element follows said introducer contour.

10. A method for treating stress urinary incontinence in a woman, comprising the steps of:
    obtaining a surgical assembly including a surgical introducer having a handle portion and a needle element extending outwardly from the handle portion to a free distal end, and a sliding mechanism including a compressible member positioned within the handle portion and a sliding button slidably coupled to the handle portion for longitudinal movement relative thereto, the sliding button having at least a first retaining device extending outwardly from a distal end thereof, the first retaining device including a projection extending outwardly therefrom to a position substantially adjacent to a proximal end of the compressible member, and substantially identical first and second sheath elements each having a proximal end, a tapered distal end region terminating in a closed tissue penetrating distal tip, a channel extending therein from an opening at the proximal end to the closed distal tip, and a side aperture defined by a peripheral edge positioned at a predetermined distance from the distal tip and extending into said channel;
    inserting the needle element into the channel of the first sheath element through the side aperture such that the distal end of the needle element is positioned within the distal end region of the first sheath element;
    exerting pressure on the sliding button to move the sliding button against the compressible member from a first resting position wherein the compressible member does not exert any force on the sliding button to the second more distal position wherein the compressible member exerts a constant force on the sliding button; engaging the retaining device with the peripheral edge of the side aperture of the first sheath element to thereby removably couple the sheath element to the introducer; and
    releasing pressure on the sliding button to thereby allow the compressible member to exert a constant force on the sliding button and first sheath element in a direction toward the first resting position.

11. The surgical assembly according to claim 10, wherein the retaining device projects outwardly and in a direction toward a proximal end of the handle.

12. The surgical assembly according to claim 11, wherein the needle element has an outer diameter of approximately 3.0 mm and the channel of the sheath element has a diameter of approximately 3.2 mm.

13. The surgical assembly according to claim 12, wherein the sheath element has an outer diameter of approximately 4.2 mm.

14. The surgical assembly according to claim 10, wherein the needle element has a tapered distal end region and the inserting step further comprises inserting the needle element until the tapered distal end region of the needle element is positioned within the tapered distal end region of the sheath element.

15. The surgical assembly according to claim 14, wherein the tapered distal end region of the needle portion has a length of approximately 1-10 mm.

16. The surgical assembly according to claim 15, wherein the tapered distal end region of the sheath element has a length of approximately 3-5 mm.

17. The surgical assembly according to claim 10, wherein the needle element is comprised of stainless steel and the sheath element is comprised of a medical grade plastic selected from the group consisting of urethane, polyethylene, and polypropylene.

18. The surgical assembly according to claim 10, wherein the needle element of the introducer has a contour, and wherein the sheath element follows said introducer contour.

\* \* \* \* \*